(12) United States Patent
Mirzadeh

(10) Patent No.: US 12,343,359 B2
(45) Date of Patent: Jul. 1, 2025

(54) INHIBITORY INTERNEURON TREATMENT METHODS, USES AND COMPOSITIONS FOR DIABETES

(71) Applicant: DIGNITY HEALTH, San Francisco, CA (US)

(72) Inventor: Zaman Mirzadeh, Phoenix, AZ (US)

(73) Assignee: DIGNITY HEALTH, San Francisco, CA (US)

( * ) Notice: Subject to any disclaimer, the term of this patent is extended or adjusted under 35 U.S.C. 154(b) by 678 days.

(21) Appl. No.: 17/613,391

(22) PCT Filed: May 18, 2020

(86) PCT No.: PCT/US2020/033368
§ 371 (c)(1),
(2) Date: Nov. 22, 2021

(87) PCT Pub. No.: WO2020/236696
PCT Pub. Date: Nov. 26, 2020

(65) Prior Publication Data
US 2022/0241343 A1     Aug. 4, 2022

Related U.S. Application Data

(60) Provisional application No. 62/851,752, filed on May 23, 2019.

(51) Int. Cl.
| | |
|---|---|
| *A61K 35/39* | (2015.01) |
| *A61K 9/00* | (2006.01) |
| *A61K 9/08* | (2006.01) |
| *A61K 35/30* | (2015.01) |
| *A61P 3/10* | (2006.01) |

(52) U.S. Cl.
CPC ............ *A61K 35/30* (2013.01); *A61K 9/0085* (2013.01); *A61K 9/08* (2013.01); *A61P 3/10* (2018.01)

(58) Field of Classification Search
None
See application file for complete search history.

(56) References Cited

U.S. PATENT DOCUMENTS

| | | |
|---|---|---|
| 7,153,684 B1 | 12/2006 | Hogan |
| 9,192,630 B2 | 11/2015 | Baraban et al. |
| 10,100,279 B2 | 10/2018 | Nicholas et al. |
| 2006/0079448 A1 | 4/2006 | Bertilsson et al. |
| 2009/0047263 A1 | 2/2009 | Yamanaka et al. |
| 2009/0068742 A1 | 3/2009 | Yamanaka |
| 2009/0191159 A1 | 7/2009 | Sakurada et al. |
| 2009/0227032 A1 | 9/2009 | Yamanaka et al. |
| 2009/0246875 A1 | 10/2009 | Yamanaka et al. |
| 2009/0304646 A1 | 12/2009 | Sakurada et al. |
| 2015/0011554 A1 | 1/2015 | Cincotta et al. |
| 2016/0008403 A1 | 1/2016 | Baraban et al. |
| 2016/0115448 A1 | 4/2016 | Studer et al. |
| 2018/0369287 A1 | 12/2018 | Nicholas et al. |
| 2019/0002826 A1 | 1/2019 | Noggle et al. |
| 2019/0062700 A1 | 2/2019 | Nicholas et al. |

OTHER PUBLICATIONS

Alvarez-Dolado, et al. "Cortical Inhibition Modified by Embryonic Neural Precursors Grafted into the Postnatal Brain," The Journal of Neuroscience, Jul. 12, 2006, 7380-7389.
Bentsen et al. "Revisiting how the brain senses glucose-and why," Cell Metabolism, Jan. 8, 2019 (Jan. 8, 2019), vol. 29, No. 1, pp. 11-17. entire document.
Casalia, et al. "Persistent seizure control in epileptic mice transplanted with GABA progenitors," Ann Neurol. Oct. 2017; 82(4): 530-542.
Chohan, et al. "Interneuron Progenitor Transplantation to Treat CNS Dysfunction," Frontiers in Neural Circuits, published Aug. 17, 2016, 1-10.
Howard, et al. "Synaptic integration of transplanted interneuron progenitor cells into native cortical networks," J Neurophysiol 116: 472-478, 2016.
Hsieh, et al. "Medial Ganglionic Eminence Progenitors Transplanted into Hippocampus Integrate in a Functional and Subtype-Appropriate Manner," eNeuro, March/Apr. 2017, 4(2) e0359-16. 2017 1-17.
Koshimizu, U., et al. "Functional requirement of gp130-mediated signaling for growth and survival of mouse primordial germ cells in vitro and derivation of embryonic germ (EG) cells" (1996) Development, 122:1235-1242.
Leksell et al., "A new fixation device for the Leksell stereotaxic system," J. Neurosurg., 66:626-629 (1987).
Leksell et al., "Stereotaxis and nuclear magnetic resonance," J. Neurol. Neurosurg. Psychiatry, 48:14-18 (1985).
Leksell et al., "Sterotaxis and Tomography, A Technical Note," Acta Neurochir., 52:1-7 (1980).
Liu, et al., "Directed differentiation of forebrain GABA interneurons from human pluripotent stem cells," Nat Protoc. Sep. 2013; 8(9):1670-1679.
Llewellyn-Smith, et al. "Long-term, dyanmic synaptic reorganization after GABAergic precursor cell transplantation into adult mouse spinal cord," J Comp Neurol., Feb. 15, 2018, 526(3): 480-495.
Maroof et al., "Directed differentiation and functional maturation of cortical interneurons from human embryonic stem cells," Cell Stem Cell May 2, 2013; 15(5):559-572.
Martinez-Cerdeno, et al. "Embryonic MGE Precursor Cells Grafted into Adult Rat Striatum Integrate and Ameliorate Motor Symptoms in 6-OHDA-Lesioned Rats," Gell Stem Cell 6, Mar. 5, 2010, 238-250.

(Continued)

*Primary Examiner* — Russell G Fiebig
(74) *Attorney, Agent, or Firm* — QUARLES & BRADY LLP

(57) ABSTRACT

Disclosed herein are compositions, methods of treatment, and uses of inhibitory interneuron precursors, derived from the brain's medial ganglionic eminence, or differentiated from iPSC or ESCs, for the treatment of pre-diabetes or diabetes. In some embodiments, compositions including inhibitory interneuron precursors are transplanted into the arcuate nucleus of the hypothalamus region of the brain, to treat, for example, diabetes, such as, type-2 diabetes, In further embodiments, inhibitory interneuron precursors are used in the manufacture of a medicament for the treatment of diabetes, for example, type-2 diabetes.

10 Claims, 2 Drawing Sheets

(56) References Cited

OTHER PUBLICATIONS

Matsui, Y., et al., "Derivation of pluripotential embryonic stem cells from murine primordial germ cells in culture." (1992) Cell 70:841.
Mirzadeh et al. "Evidence That Arcuate Nucleus Neurocircuit Remodeling Ameliorates Hyperglycemia In Type 2 Diabetes," Diabetes, Jun. 4, 2019 (Jun. 4, 2019), vol. 68, Suppl 1, p. 1 of 1. entire document.
Mirzadeh et al. "Perineuronal Net Formation during the Critical Period for Neuronal Maturation in the Hypothalamic Arcuate Nucleus," Nature Metabolism, Jan. 21, 2019 (Jan. 21, 2019), vol. 1, Iss. 2, pp. 212-221. entire document.
Nicholas et al., "Functional Maturation of hPSC-Derived Forebrain Interneurons Requres an Extended Timeline and Mimics Human Neural Development," Cell Stem Cell May 2, 2013, 12(5): 573-586.
Shamblott, M., et al. "Derivation of pluripotent stem cells from cultured human primordial germ cells," Nov. 1998, Proc. Natl. Acad. Sci. USA, 95:13726-13731.
Shamblott, M., et al. "Human embryonic germ cell derivates express a broad range of developmentally distinct markers and proliferate extensively in vitro," Jan. 2, 2001, Proc. Natl. Acad. Sci. USA 98: 113-118.
Shetty, et al. "GABA-ergic Cell Therapy for Epilepsy: Advances, Limitations and Challenges," Neurosci Biobehav Rev. Mar. 2016, 62: 35-47.
Shetty, et al. "Potential of GABA-ergic cell therapy for schizophrenia, neuropathic pain, and Alzheimers and Parkinsons diseases," Brain Res., May 1, 2016, 1638(Pt. A): 74-87.
Upadhya et al., "Neural Stem Cell or Human Induced Pluripotent Stem Sell-derived GABA-ergic Progenitor Cell Grafting in an Animal Model of Chronic Temporal Lobe Epilepsy," Curr Protoc Stem Cell Biol (2016) 38:2D.7.1-2D.7.47.
Vazin, et al., "Human embryonic stem cells: Derivation, culture, and differentiation: A review," Restor Neurol Neurosci. Jan. 1, 2010; 28(4):589-603.
Vogt, et al. Viral-mediated Labeling and Transplantation of Medial Ganglionic Eminence (MGE) Cells for In Vivo Studies, Journal of Visualized Experiments, published Apr. 2015, 1-12.
International Search Report and Written Opinion for PCT/US2020/033368, mailed Aug. 17, 2020 (9 pages).

INHIBITORY INTERNEURON TREATMENT METHODS, USES AND COMPOSITIONS FOR DIABETES

CROSS REFERENCE TO RELATED APPLICATIONS

This application represents the national stage filing of PCT/US2020/033368, filed May 18, 2020, which claims the benefit of U.S. Application No. 62/851,752, filed on May 23, 2019. The content of each application is incorporated herein by reference in its entirety.

TECHNICAL FIELD

Provided herein are methods, compositions, and systems useful for the treatment of diabetes, alleviation or amelioration of the symptoms of diabetes, and/or for the prevention of diabetes or its symptoms, in a subject in need thereof. In some embodiments, the diabetes is type 2 diabetes. In particular, the methods, compositions, and systems disclosed herein are useful for treating hyperglycemia in a subject diagnosed with, or suspected of having, diabetes.

BACKGROUND

Type 2 diabetes (T2D) is among the most common and costly diseases in the world today, and current medical therapies have failed to curtail the epidemic and its associated complications, including obesity, cardiovascular disease, kidney disease, and stroke.

The diabetes problem is currently addressed using a variety of anti-diabetic medications, both oral and parenteral, acting via different mechanisms but mostly targeting peripheral insulin-producing or insulin-sensitive tissues. Over 40 new antidiabetic drugs have been introduced since 2005 without a concomitant improvement in outcomes for patients with diabetes. This emphasizes the need for interventions that address the underlying cause rather than the manifestation (hyperglycemia) of diabetes to make a meaningful impact on the disease.

SUMMARY

Embodiments of the current technology relate to compositions and methods for utilizing inhibitory interneurons and/or inhibitory interneuron precursors to treat diabetes in a subject in need thereof. More specifically, embodiments herein relate to delivering inhibitory interneuron precursor compositions into the arcuate nucleus of the hypothalamus and/or into structures adjacent to or surrounding the arcuate nucleus, such as the mediobasal hypothalamus and the ventromedial hypothalamus, of a subject that has been diagnosed with, or is suspected of having, diabetes or pre-diabetes.

In some embodiments, the inhibitory interneuron precursors are embryonic inhibitory interneuron precursors, derived from the brain's medial ganglionic eminences. In other embodiments, the inhibitory interneuron precursors are derived, for example, from embryonic stem cells, induced pluripotent stem cells, or neural precursor or progenitor cells.

In some embodiments, compositions comprising inhibitory interneurons and/or inhibitory interneuron precursors are used for the treatment of diabetes, for example, type 2 diabetes. In other embodiments, inhibitory interneurons and/or inhibitory interneuron precursors are used in the manufacture of a medicament for the treatment of diabetes, for example, type 2 diabetes. In some embodiments, methods comprising administering inhibitory interneurons and/or inhibitory interneuron precursors, and/or compositions or medicaments comprising inhibitory interneurons and/or inhibitory interneuron precursors to a subject in need thereof are provided herein, for example, to treat type 2 diabetes.

These and other aspects are further described in the drawings and written description that follow.

BRIEF DESCRIPTION OF DRAWINGS

The technology disclosed herein will be better understood from a reading of the following detailed description taken in conjunction with the drawings in which like reference designators are used to designate like elements, and in which:

FIGS. 1(A) and (B). In FIG. 1 part (B) metabolic phenotyping data is presented showing blood glucose, daily weight gain, and food intake values for diabetic ob/ob mice, transplanted with vehicle control or MGE inhibitory interneurons, prior to and at successive days after transplant (DAT). There was a significant reduction in blood glucose in MGE-transplanted ob/ob mice compared to vehicle control.

FIGS. 2(A), (B) and (C).

DESCRIPTION OF THE INVENTION

Definitions and Terminology

Figure 1:
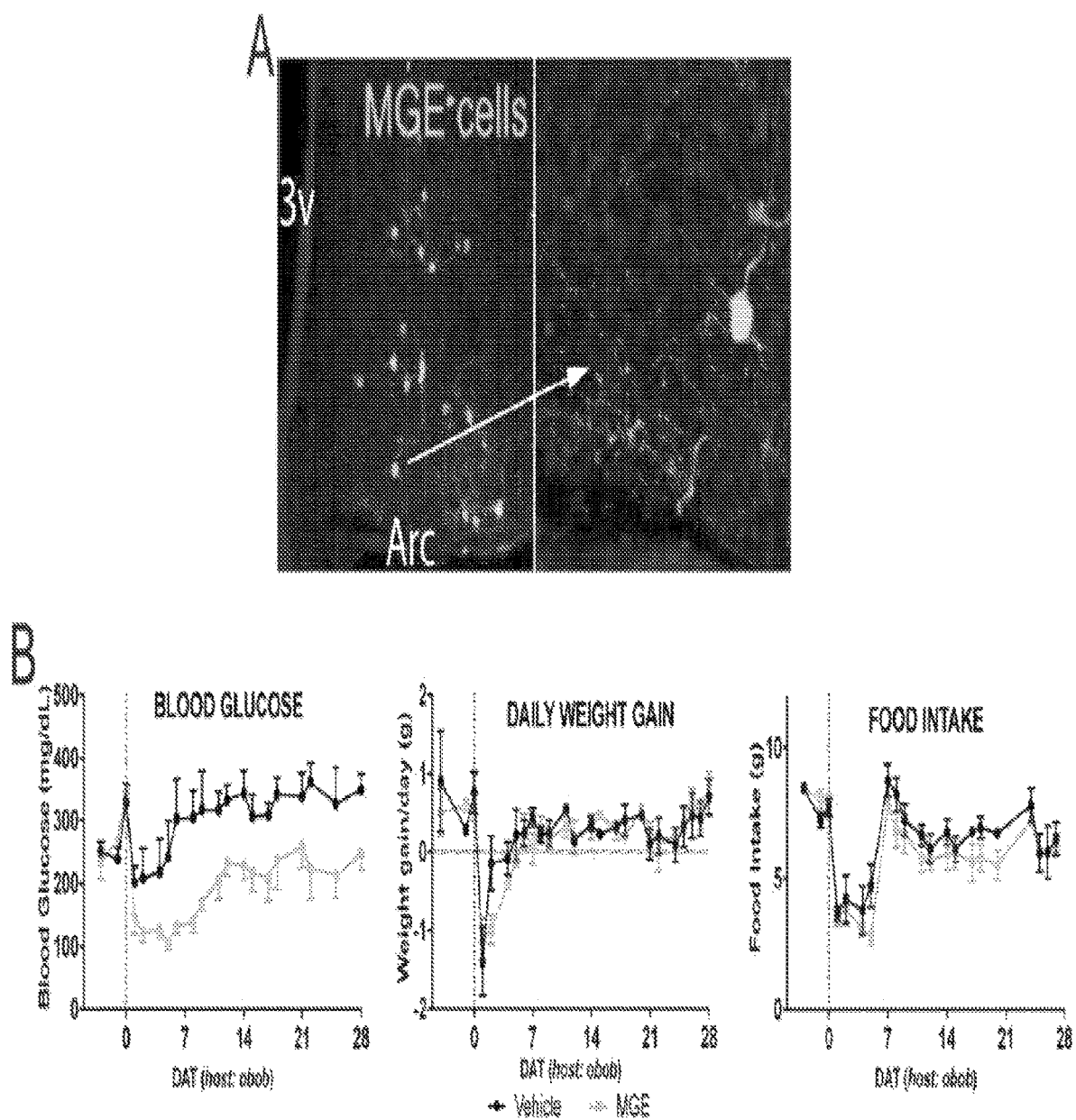
FIG. 1 depicts in part (A) a low power confocal image (left) shows the distribution of green fluorescent protein+ (GFP+) medial ganglionic eminence (MGE) cells transplanted into the arcuate nucleus (Arc), situated adjacent to the wall of the 3rd ventricle (3v). Higher power confocal image (right) shows extensive processes of transplanted MGE cells intercalating among host Arcuate cells.
Figure 2:
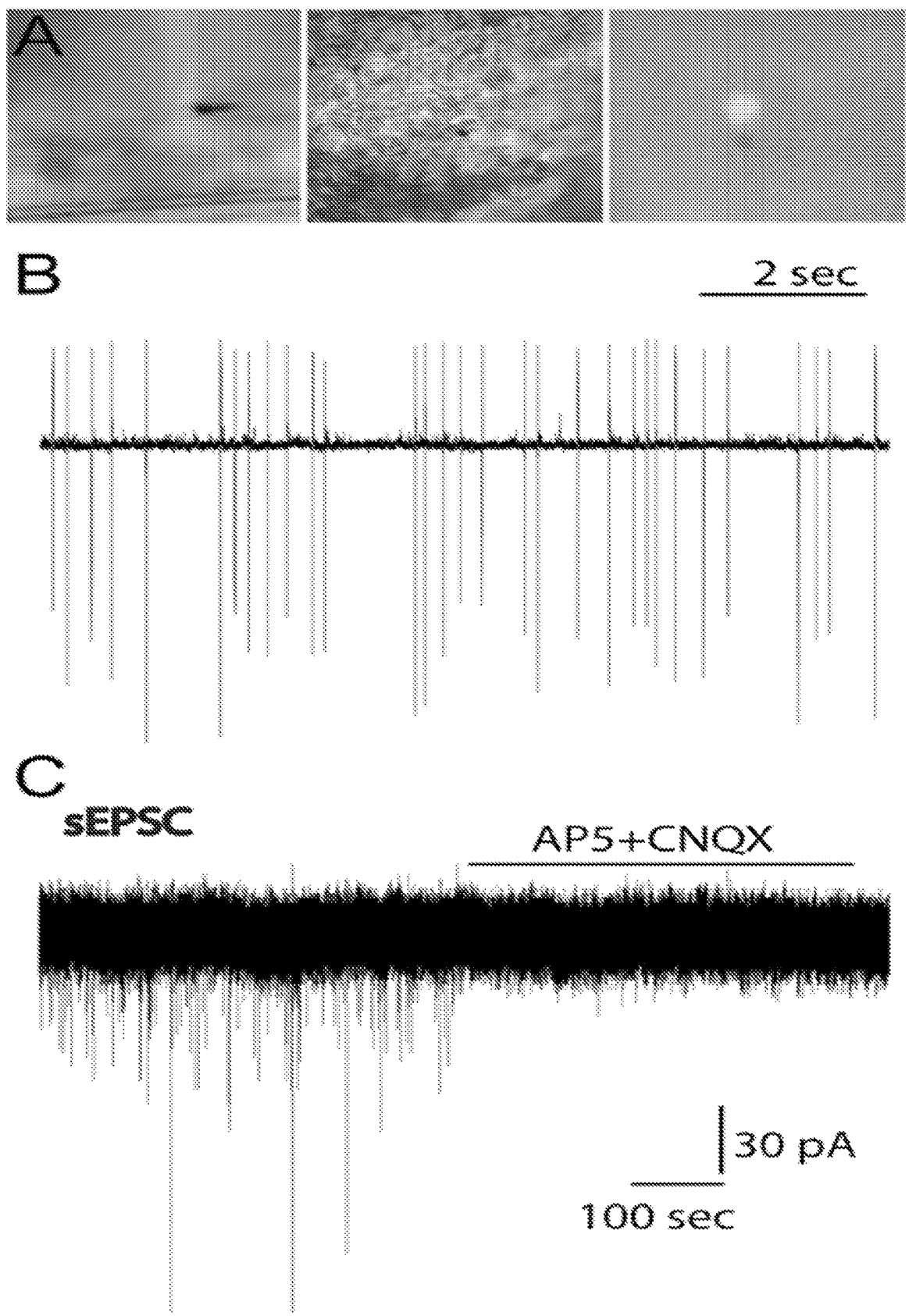
FIG. 2 shows in part (A) a low- (left) and high- (middle) magnification differential interference contrast and high magnification fluorescent (right) microscope images show a GFP+ MGE cell in the arcuate nucleus with an adjacent glass pipette used for slice recording at 30 days after transplant. The recordings, which are in cell-attached mode in (B), showing spontaneous firing activity, and in patched whole-cell recording in (C), showing spontaneous excitatory postsynaptic currents (sEPSCs) (blocked by glutamatergic receptor antagonists AP5 and CNQX), reveal that GFP+ MGE cells transplanted into the arcuate nucleus are functional and receive synaptic glutamatergic inputs from neighboring host cells.

The disclosed compositions and methods may be further described using definitions and terminology as follows. The definitions and terminology used herein are for the purpose of describing particular embodiments only, and are not intended to be limiting.

The technology disclosed herein is described in one or more exemplary embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

As used in this specification and the claims, the singular forms "a," "an," and "the" include plural forms unless the context clearly dictates otherwise. For example, the term "a cell" or "an inhibitory interneuron" should be interpreted to mean "one or more cells" and "one or more inhibitory interneurons," respectively, unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or "B" or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, "marker" refers to any molecule that can be measured or detected. For example, a marker can include, without limitations, a nucleic acid, such as, a transcript of a gene, a polypeptide product of a gene, a glycoprotein, a carbohydrate, a glycolipid, a lipid, a lipoprotein, a carbohydrate, or a small molecule.

As used herein, "expression" and grammatical equivalents thereof, in the context of a marker, refers to production of the marker and may also refer to the level or amount of the marker. For example, expression of a marker or presence of a marker in a cell or a cell that is positive for a marker, refers to expression of the marker at a level that is similar to a positive control level. The positive control level may be determined by the level of the marker expressed by a cell known to have the cell fate associated with the marker. Similarly, absence of expression of a marker or a cell that is negative for a marker, refers to expression of the marker at a level that is similar to a negative control level. The negative control level may be determined by the level of the marker expressed by a cell known to not have the cell fate associated with the marker.

The terms "enriching" or "enriched" are used interchangeably herein and mean that the yield (fraction) of cells of one type is increased by at least 10% over the fraction of cells of that type in the starting culture or preparation.

The phrase "differentiation factor(s)" as used herein refers to the agent(s) that are included in the medium for culturing cells of the present disclosure, which agent(s) promote the differentiation of the cells from a first cell type to a second cell type, where the second cell type is differentiated compared to the first cell type.

In the context of cell ontogeny, the adjective "differentiated" is a relative term. A "differentiated cell" is a cell that has progressed further down the developmental pathway than the cell it is being compared with. Thus, pluripotent embryonic stem cells can differentiate to lineage-restricted precursor cells. These in turn can be differentiated further to cells further down the pathway, or to an end-stage differentiated cell, such as GABAergic interneurons.

By "pluripotent stem cell" or "pluripotent cell" it is meant a cell that has the ability under appropriate conditions of producing progeny of several different cell types that are derivatives of all of the three germinal layers (endoderm, mesoderm, and ectoderm). Pluripotent stem cells are capable of forming teratomas. Examples of pluripotent stem cells are embryonic stem (ES) cells, embryonic germ stem (EG) cells, embryonal carcinoma stem (EC) cells, and induced pluripotent stem (iPS) cells. PS cells may be from any organism of interest, including, e.g., human; primate; non-human primate; canine; feline; murine; equine; porcine; avian; camel; bovine; ovine, and so on.

As used herein, the term "embryonic stem cell" or "ES cell" refers to a cell that a) can self-renew, b) can differentiate to produce all types of cells in an organism, and c) is derived from a developing organism or is an established ES cell line which was derived from a developing organism. ES cell may be derived from the inner cell mass of the blastula, or from the epiblast, of a developing organism. ES cell may be derived from a blastomere generated by single blastomere biopsy (SBB) involving removal of a single blastomere from the developing organism. In general, SBB provides a non-destructive alternative to inner cell mass isolation. SBB and generation of hES cells from the biopsied blastomere is described in Cell Stem Cell, 2008 Feb. 7; 2(2):113-7. ES cells can be cultured over a long period of time while maintaining the ability to differentiate into all types of cells in an organism. In culture, ES cells typically grow as flat colonies with large nucleo-cytoplasmic ratios, defined borders and prominent nucleoli. In addition, hES cells express SSEA-3, SSEA-4, TRA-1-60, TRA-1-81, and Alkaline Phosphatase, but not SSEA-1. Examples of methods of generating and characterizing ES cells are well known in the art. For an overview, see e.g., Vazin and Freed, *Restor Neurol Neurosci.* 2010 Jan. 1; 28(4):589-603; *Human Stem Cell Manual, a Laboratory Guide*, Jeanne F. Loring and Suzanne E. Peterson, 2nd ed., 2012; *Handbook of Stem Cells*, Anthony Atala and Robert Lanza, 2nd ed., 2012. Examples of ES cells include naive ES cells.

As used herein, the term "embryonic germ stem cell," embryonic germ cell" or "EG cell" refers to a cell that a) can self-renew, b) can differentiate to produce all types of cells in an organism, and c) is derived from germ cells and germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

As used herein, the term "induced pluripotent stem cell" or "iPS cell" refers to a cell that a) can self-renew, b) can differentiate to produce all types of cells in an organism, and c) is derived from a somatic cell. iPS cells have an ES cell-like morphology, growing as flat colonies with large nucleo-cytoplasmic ratios, defined borders and prominent nucleoli. In addition, iPS cells express one or more key pluripotency markers known by one of ordinary skill in the art, including but not limited to Alkaline Phosphatase, SSEA3, SSEA4, Sox2, Oct3/4, Nanog, TRA 160, TRA 181, TDGF 1, Dnmt3b, FoxD3, GDF3, Cyp26a1, TERT, and zfp42. iPS cells may be generated by providing the somatic cell with "reprogramming factors," i.e., one or more, e.g., a cocktail, of biologically active factors that act on a cell to alter transcription, thereby reprogramming a cell to pluripotency. Examples of methods of generating and characterizing iPS cells may be found in, for example, Application Nos. US20090047263, US20090068742, US20090191159, US20090227032, US20090246875, and US20090304646, the disclosures of which are incorporated herein by reference.

As used herein, the term "somatic cell" refers to any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e., ectoderm, mesoderm, and endoderm. For example, somatic cells would include both neurons and neural progenitors, the latter of which may be able to self-renew and naturally give rise to all or some cell types of the central nervous system but cannot give rise to cells of the mesoderm or endoderm lineages.

The term "cell line" refers to a population of largely or substantially identical cells that has typically been derived from a single ancestor cell or from a defined and/or substantially identical population of ancestor cells. The cell line may have been or may be capable of being maintained in culture for an extended period (e.g., months, years, for an unlimited period of time).

The term "precursor cell" as used herein, is a cell capable of differentiating into lineage-committed cells that populate the body. Such cells may be pre- or post-mitotic, and include but are not limited to progenitor cells and cells with an established neural fate that have not fully completed differentiation and/or integration into the endogenous host tissue.

The terms "inhibitory precursor cell" and "inhibitory interneuron precursor cell" as described herein refer to a cell that is capable of migrating and differentiating into a GABA-producing inhibitory interneuron in vitro or in vivo. Such cells may arise, e.g., from the MGE, CGE, LGE or another part of the mammalian brain. Such cells may also be differentiated from or reprogrammed from other cell types. In some embodiments, an inhibitory interneuron precursor cell comprises an MGE precursor cell.

"Inhibitory interneurons," "inhibitory neurons," and "GABAergic neurons," refer to a specialized type of neuron whose primary role is to form a connection between other types of neurons. They are neither sensory nor motor neurons and they function to modulate neural circuitry and circuit activity. Inhibitory interneurons characteristically release the neurotransmitters gamma-am inobutyric acid (GABA) and glycine. Within the overarching categorization of GABAergic interneurons there are also numerous interneuron subtypes that are largely categorized based on the surface markers they express. Three major subtypes, categorized based on the calcium-binding protein expressed are parvalbumin (PV)-expressing interneurons, somatostatin (SST)-expressing interneurons, and 5HT3a (5HT3aR)-expressing interneurons. Inhibitory interneurons account for about 20% of neurons in the cerebral cortex. Most cortical interneurons originate in the medial ganglionic eminence (MGE) of the developing ventral telencephalon region of the brain.

Throughout embryogenesis, interneurons are primarily generated in a structure broadly termed the ganglionic eminence (GE). The GE is a transitory brain structure located in the ventral area of the telencephalon, and is anatomically present during embryonic development. The GE becomes evident at approximately E11.5 in the developing murine system. In total, there are three ganglionic eminences: the medial ganglionic eminence, (MGE), the caudal ganglionic eminence (CGE), and the lateral ganglionic eminence (LGE). As embryonic development continues, the GEs grow and ultimately fuse, at which point they are no longer present in the mature brain. In humans, the GEs disappear by about one year of age. The MGE and the CGE are the primary sources of cortical interneurons in the developing nervous system.

As used herein, "medial ganglionic eminence (MGE) precursor cell(s)," "MGE neural precursor cells," and "MGE precursor cells" refer to a population of mitotic and post-mitotic inhibitory interneuron precursor cells that express the homeobox gene NKX2.1. Other markers useful in the identification of MGE precursor cells include, but are not limited to one or more of the LIM-homeobox genes LHX6, LHX8, or LHX7, the telencephalic transcription factors FOXG1, OLIG2, DLX1/2 and ASCL1. In some embodiments, expression of NKX2.1 and FOXG1 is indicative of MGE precursor cells. Additionally or alternatively, in some embodiments, MGE precursor cells do not detectably express PAX6. In general, MGE precursor cells are capable of differentiating into GABA-expressing, inhibitory interneurons under suitable differentiation conditions (e.g., in culture, or after implantation into a host arcuate nucleus region of the hypothalamus). MGE precursor cells can be harvested, for example, from the MGE region of the embryonic brain, or can be differentiated from or reprogrammed from other cell types. See e.g., Upadhya et al., *Curr Protoc Stem Cell Biol* (2016) 38:2D.7.1-2D.7.47; Liu, et al., *Nat Protoc.* 2013 (September); 8(9):1670-1679; Maroof et al., *Cell Stem Cell* 2013 May 2; 15(5):559-572; Nicholas et al., *Cell Stem Cell* 2013 May 2, 12(5): 573-586, and U.S. Pat. No. 10,100,279, which are incorporated herein by reference in their entireties.

The term "isolated" in context of cells or a cell population refers to cells that are in an environment other than their native environment, such as, apart from tissue of an organism.

The neural precursor cell populations disclosed herein can be isolated from human tissue (e.g., human fetal cortex or human ganglionic eminences), or can be differentiated from stem cells or other multipotent cells. Thus, in some embodiments, the neural precursor cell populations are isolated from a source of pluripotent stem cells. In some embodiments, the neural precursor cells are differentiated from human stem cells, e.g., human embryonic stem cells. In other embodiments, the neural precursor cells are differentiated from induced pluripotent stem cells. In yet other embodiments, the neural precursor cells are differentiated from neural stem cells. In yet other embodiments, the neural precursor cell populations are created through reprogramming of cells, e.g., neural cells obtained from the MGE, cortex, sub-cortex, other regions of the brain, or non-neural cells (see e.g., U.S. 20180369287 and US20190062700; herein incorporated by reference in their entirety). In some embodiments, the neural precursor cells are MGE precursor cells.

Compositions

Disclosed herein are compositions comprising inhibitory interneuron precursor cells. In some embodiments, the inhibitory interneuron precursor cells comprise MGE precursor cells. In some embodiments, the MGE precursor cells are harvested from embryonic brain tissue. In some embodiments, the MGE precursor cells are differentiated from ESCs or iPSCs in culture. The embryonic brain tissue, the ESCs, or iPSCs may be derived from a vertebrate, mammal, primate, mouse, rat, pig, bovine, ovine, avian, dog, cat, or human. In some embodiments, the inhibitory neuronal precursor cells are differentiated from, or derived from, the subject's own tissues or cells.

In some embodiments, the compositions of the present disclosure include a population of cells in which at least about 70%, 75%, 80%, 85%, 90%, 95%, 96%, 97%, 98% 99% or 100% of the population includes the desired cell type. By way of example, if cells are harvested from embryonic brain tissue, a composition comprising at least about 70% MGE precursor cells would include at least about 70% MGE precursor cells; about 30% of the cells or less may include, for example, cells from other regions of the brain (e.g., the lateral ganglionic eminence) that were intentionally or unintentionally harvested. As another example, if cells are differentiated from iPSCs or ESCs, a composition comprising at least about 70% MGE precursor cells may include at least about 70% MGE precursor cells; about 30% of the cells or less may include, for example, precursors to the MGE precursor cells, or cells that have differentiated to assume characteristics that distinguish them from MGE precursor cells (e.g., cells that have differentiated to inhibitory interneurons.

In some embodiments, the compositions include inhibitory interneuron precursor cells comprising between about 5000 to about 7000 cells, between about 7000 to about 10,000 cells, between about 10,000 to about 12,000 cells, between about 12,000 to about 15,000 cells, between about 15,000 cells to about 17,000 cells, between about 17,000 cells to about 20,000 cells, or more than about 20,000 cells. In some embodiments, compositions comprise between about 20,000-about 0.05 million cells, between about 0.05 million to about 1 million cells, between about 1-2 million cells, or between about 1-5 million cells. In some embodiments, compositions comprise between about 20,000 cells and about 100,000 cells, between about 30,000 cells and about 90,000 cells, between about 40,000 cells and about 80,000 cells, between about 50,000 cells and about 70,000 cells or about 60,000 cells. In some embodiments, the cells in the composition comprise at least about 70%, 75%, 80%, 85%, 89%, 90%, 91%, 92%, 93%, 94%, 95%, 96%, 97, 98%, or 99% viable/live cells.

In some embodiments, the cells are suspended in serum-free medium and can be stored (e.g., frozen at −70° C.) or administered, e.g., via injection into the desired region of the brain (e.g., into the arcuate nucleus). In some embodiments, the compositions comprising the cells are provided in a dosage volume of about 10 to about 1000 nl, or about 10, about 20, about 30, about 40, about 50, about 60, about 70, about 80, about 90, about 100, about 200, about 300, about 500, or about 1000 nl. In some embodiments, the cells are suspended in serum-free medium and the compositions are provided in a volume of about 10 to about 1000 µl, or about 10, about 20, about 30, about 40, about 50, about 60, about 70, about 80, about 90, about 100, about 200, about 300, about 500, or about 1000 µl. In some embodiments, the cells are suspended in serum-free medium and the compositions are provided in a volume of about 1-2 ml, about 1-5 ml, or about 5-10 ml.

In some embodiments, the compositions comprise inhibitory interneuron precursor cells in a semi-solid or solid support matrix.

In some embodiments, the cells are suspended in a medium compatible with long-term storage, e.g., freezing.

In some embodiments, compositions disclosed herein include, in addition to inhibitory interneuron precursor cells, additional factors, such as one or more differentiation factors, cell signaling molecules, nutritional supplements, salts, buffers, and the like. Exemplary additional factors include, but are not limited to hormones, growth factors, and transcription factors. In some embodiments, the neuronal precursor cells are incubated with one or more differentiation factors prior to administration. In some embodiments, the differentiation factors act to direct the inhibitory neuronal precursor cells toward maturation, e.g., as a GABAergic inhibitory interneuron, or act to slow differentiation and maturation.

In some embodiments, a pharmaceutically acceptable carrier may be used with the compositions herein. The terms "pharmaceutically acceptable" refer to compounds and compositions that are suitable for administration to humans and/or animals without undue adverse side effects (such as toxicity, irritation, and/or allergic response) commensurate with a reasonable benefit/risk ratio. An exemplary carrier may be sterile saline, an alcohol, propylene glycol, and many others known in the art.

Methods

Embodiments of the technology disclose compositions, uses, and treatment methods whereby inhibitory precursor interneurons, or inhibitory interneurons are delivered into the arcuate nucleus of the hypothalamus, and/or into the mediobasal hypothalamus, including the ventromedial hypothalamus, region of the brain and may be used to provide a long-lasting treatment for subjects with diseases or conditions characterized by hyperglycemia, such as diabetes. In some embodiments, the inhibitory precursor neurons comprise MGE precursor cells.

The term "diabetes mellitus" or "diabetes" refers to a disease or condition that is generally characterized by metabolic defects in the production and activity of insulin, the hormone that regulates glucose utilization, resulting in the failure to maintain appropriate blood sugar levels in the body. The result of these defects is elevated blood glucose, referred to as "hyperglycemia." Two major forms of diabetes are type 1 diabetes and type 2 diabetes. Type 1 diabetes is generally the result of an absolute deficiency of insulin. Type 2 diabetes often occurs in the face of normal, or even elevated levels of insulin and can result from the inability of tissues to respond appropriately to insulin. Most type 2 diabetic patients are insulin resistant and have a relative deficiency of insulin, in that insulin secretion cannot compensate for the resistance of peripheral tissues to respond to insulin. In addition, many type 2 diabetics are obese. Other types of disorders of glucose homeostasis include "pre-diabetes," i.e., impaired glucose tolerance, which is a metabolic stage intermediate between normal glucose homeostasis and diabetes, and gestational diabetes mellitus, which is glucose intolerance in pregnancy in women with no previous history of type 1 or type 2 diabetes.

Growing evidence suggests that T2D is fundamentally a disorder of central nervous system (CNS) control over glycemia, such that interventions targeting the CNS may be more effective in producing diabetes remission.

The term "metabolic syndrome" refers to a cluster of metabolic abnormalities including abdominal obesity, insulin resistance, glucose intolerance, diabetes, hypertension and dyslipidemia. These abnormalities are known to be associated with an increased risk of vascular events.

In addition to diabetes and metabolic syndrome, several other diseases or conditions result in, or are associated with hyperglycemia, including but not limited to pancreatitis, pancreatic cancer, hyperthyroidism, Cushing's syndrome, tumors that secrete hormones, including glucagonoma, pheochromocytoma, or growth hormone-secreting tumors; certain medication, such as prednisone, estrogens, beta-blockers, glucagon, oral contraceptives, phenothiazines.

As used herein, the term "hyperglycemia" refers to a condition in which a subject's blood sugar level is above normal. Hyperglycemia is typically diagnosed by a blood test. Exemplary blood tests include, but are not limited to the following. (i) A random blood glucose test: this test reflects the blood sugar level at a given point in time. (ii) A fasting blood glucose test: this is a measurement of blood sugar level taken in the early morning prior to eating or drinking anything since the night before. Normal fasting blood glucose levels are less than 100 mg/dL. Levels above 100 mg/dL up to 125 mg/dL suggest prediabetes, while levels of 126 mg/dL or above are diagnostic of diabetes. (iii) An oral glucose tolerance test: this is a test that measures blood glucose levels at given time points after a dose of sugar is consumed. This test is most commonly used to diagnose gestational diabetes. Typically, a normal blood glucose tolerance level is lower than 140 mg/dL (7.8 mmol/L). A blood glucose level between 140 and 199 mg/dL (7.8 and 11 mmol/L) is considered impaired glucose tolerance. A blood glucose level of 200 mg/dL (11.1 mmol/L) or higher may indicate diabetes or other condition in which hyperglycemia is a symptom. (iv) A glycohemoglobin A1c test: this test is a measurement of glucose that is bound to red blood cells and provides an indication about blood sugar levels over the past 2 to 3 months. For someone who doesn't have diabetes, a normal A1C level is typically below 5.7 percent. If the A1C level is between 5.7 and 6.4 percent, the subject is considered to have impaired fasting glucose, which correlates with a high risk of developing diabetes in the future. An A1C level of 6.5 percent or higher on two separate occasions shows that the subject has diabetes or other disease or condition in which persistent, or persistent variable hyperglycemia is a symptom. An A1C level above 8 percent means that the subject's blood sugar is not well-controlled and that the subject is at higher risk of developing complications of hyperglycemia. By way of example, for most adults who have diabetes, an A1C level of 7 percent or less is a common treatment target. Lower or higher targets may be appropriate for some individuals.

Symptoms of hyperglycemia include increased thirst and a frequent need to urinate, headaches, tiredness, blurred vision, hunger and trouble thinking or concentrating. Severely elevated blood sugar levels can result in coma. Over time, hyperglycemia can lead to damage to organs and tissues. Long-term hyperglycemia can impact the body in several ways, including but not limited to: impairment of the immune response, leading to poor healing of cuts and wounds; nerve damage that can lead to burning, tingling, pain, and changes in sensation; vision problems and eye damage, including damage to the retina, glaucoma, and cataracts; gum disease; damage to the heart and blood vessels that can increase the risk of heart attack, stroke, and peripheral artery disease; damage to the kidneys eventually leading to kidney failure.

In some embodiments, subjects or patients exhibit persistent, hyperglycemia, or persistent variable hyperglycemia. In some embodiments, subjects or patients exhibit, in addition to elevated blood glucose levels, one or more of the symptoms of hyperglycemia. In some embodiments, subject or patients having hyperglycemia have been diagnosed or are suspected of having diabetes, or a disease or condition associated with hyperglycemia.

The arcuate nucleus of the hypothalamus (also known as ARH, ARC, or infundibular nucleus) is an aggregation of neurons in the mediobasal hypothalamus, adjacent to the third ventricle and the median eminence. The arcuate nucleus includes several important and diverse populations of neurons that help mediate different neuroendocrine and physiological functions. The populations of neurons found in the arcuate nucleus are based on the hormones they secrete or interact with. These populations of neurons are responsible for hypothalamic function, such as regulating hormones released from the pituitary gland or secreting their own hormones.

Neurons in the arcuate nucleus are also responsible for integrating information and providing inputs to other nuclei in the hypothalamus or inputs to areas outside this region of the brain. The function of the arcuate nucleus relies on its diversity of neurons, but its central role is involved in homeostasis. The arcuate nucleus provides many physiological roles involved in feeding, metabolism, fertility, and cardiovascular regulation.

The ventromedial hypothalamus (or the ventromedial nucleus of the hypothalamus) is a nucleus directly adjacent to the arcuate nucleus with a position that is just dorsolateral to the arcuate nucleus. The ventromedial hypothalamus refers to a distinct, morphological nucleus of the hypothalamus involved in terminating hunger (the feeling of fullness), glucose homeostasis, fear, thermoregulation, sexual activity.

Without wishing to be bound by theory, embodiments herein address a common underlying feature present in both type 1 and type 2 diabetes, which is abnormal hyperactivity of a group of arcuate nucleus neurons that co-express agouti-related peptide (Agrp) and neuropeptide Y (NPY). The premise is that the provided inhibitory precursor interneurons, and/or inhibitory interneurons, results in reduction of this abnormal hyperactivity and thereby the amelioration of hyperglycemia. Importantly, there is the prospect of a long-lasting reduction in hyperglycemia that is very different from currently available medical therapies, which are reliant on and only effective with repeated drug administration to keep blood glucose in the normal range.

In view of the above, the treatment methods contemplated herein include administering to an animal, preferably a human patient, having diabetes or pre-diabetes or other disease or condition characterized by hyperglycemia, a composition, wherein the composition comprises one or more inhibitory interneuron precursor cells, to the arcuate nucleuse of the hypothalamus, and/or to structures or regions immediately adjacent to or surrounding the arcuate nucleus, in an amount effective to treat diabetes, pre-diabetes or other disease or conditions characterized by hyperglycemia. In some embodiments, the composition is administered into one or more of the arcuate nucleus, the mediobasal hypothalamus, and the ventromedial hypothalamus. In other embodiments, use of one or more inhibitory interneuron precursor cells for the treatment of diabetes, for example, type-2 diabetes, is contemplated. In other embodiments, inhibitory interneuron precursor cells are used in the manufacture of a medicament for the treatment of diabetes, for example, type-2 diabetes.

The terms "treatment," "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease. By way of example, but not by way of limitation, a subject may be diagnosed with a disease or condition characterized by increased blood glucose levels, such as diabetes, or metabolic syndrome. In some embodiments, while the subject's blood glucose levels may fluctuate over time, a persistent risk of hyperglycemia exists that is threat to the health of the subject. Accordingly, in some embodiments, a subject may be treated according to the present methods during a time or relatively stable or normal blood glucose levels, or may be treated during a time of hyperglycemia. By way of example, treatment is effective if the subject's blood sugar levels exhibits a statistically relevant decrease from pre-treatment levels.

The term "effective amount" refers to an amount of an active agent or cell population that is sufficient to exhibit a detectable therapeutic effect without excessive adverse side effects (such as toxicity, irritation, and allergic response) commensurate with a reasonable benefit/risk ratio when used in the manner of the present disclosure. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, the effective amount for a given situation can be determined by one of ordinary skill in the art using the knowledge in the art, and routine experimentation based on the information provided herein.

The optimum dosing regimen can be determined by one skilled in the art without undue experimentation. For example (but not by way of limitation), the compositions disclosed herein may be prepared for intravenous (i.v.) injection with modified antibodies or transport proteins that assist in uptake into the brain despite the blood-brain barrier, transplantation, and administration or injection through a needle, catheter, or tube.

By way of example, but not by way of limitation, in some embodiments, a subject receives a single administration of an inhibitory precursor cell composition via injection into the desired region of the brain (e.g., the arcuate nucleus, and/or the surrounding mediobasal hypothalamus, and/or the ventromedial hypothalamus). In some embodiments, a subject receives multiple administrations of an inhibitory precursor cell composition. By way of example, a subject may receive multiple administrations on the same date, at the same site or at sites a small distance apart from each other, e.g., to target different regions of the arcuate nucleus and/or surrounding structures (e.g., mediobasal hypothalamus, ventromedial hypothalamus) or to ensure that at least some of the cells are injected into at least one region of the arcuate nucleus and/or surrounding structures. Thus, in some embodiments, a subject may receive 1, 2, 3, 4, 5, 6, 7, 8, 9, or 10 different administrations on the same day, targeting the same site or different sites, e.g., target sites separated by about 1 µm or less, about 1-3 µm, about 1-5 µm, about 1-10 µm, about 10-20 µm, about 10-50 µm, about 50-100 µm, about 100-500 µm, or about 500-1000 µm. In some embodiments, the different target sites are separated by about 1 mm, 2 mm, 3 mm, 4 mm, 5 mm, 6 mm, 7 mm, 8 mm 9 mm, 10 mm, 2 cm, 3 cm, 4 cm 5 cm, 6 cm, 7 cm, 8 cm, 9 cm, or by about 10 cm. In some embodiments, a subject may receive multiple administrations on different dates, e.g., a first administration on day 0, followed by one or more administrations on a different date, e.g., on day 1, 2, 5, 7, 10 or day 14. In some embodiments, a treatment regimen provides for a treatment once per month, once per year, once every other year, or once every 5 years; a treatment regimen may include multiple administrations. In some embodiments, a subject receives more than one dose at a single time (e.g., at different sites at the same time).

In some embodiments, a single administration comprises a dose of inhibitory precursor cells comprising between about 5000 to about 7000 cells, between about 7000 to about 10,000 cells, between about 10,000 to about 12,000 cells, between about 12,000 to about 15,000 cells, between about 15,000 cells to about 17,000 cells, between about 17,000 cells to about 20,000 cells, or more than about 20,000 cells. In some embodiments, compositions comprise between about 20,000 cells and about 100,000 cells, between about 30,000 cells and about 90,000 cells, between about 40,000 cells and about 80,000 cells, between about 50,000 cells and about 70,000 cells or about 60,000 cells. In some embodiments, the cells in a single dose comprise at least about 70%, 75%, 80%, 85%, 89%, 90%, 91%, 92%, 93%, 94%, 95%, 96%, 97, 98%, or 99% viable/live cells. Methods of determining cell viability are well known in the art, and kits for doing so are commercially available.

In some embodiments, the cells are suspended in serum-free medium and administered, via injection into the desired region of the brain (e.g., the arcuate nucleus) in a volume of about 10 nl-50 µl per dose, 10 nL-100 µl per dose, or from between about 10 nL-1000 µl per dose. In some embodiments, cells are administered in a volume of between about 10-50 nl, 50-100 nl, 100-500 nl, or between about 500-1000 nl per dose. In some embodiments, cells are administered in a volume of between about 10-10 µl, 20-40 µl, 40-60 µl, 50-100 µl, 100-500 µl or 500-1000 µl per dose. In some embodiments, cells are administered in a volume of about 10, about 20, about 30, about 40, about 50, about 60, about 70, about 80, about 90, about 100, about 200, about 300, about 500, or about 1000 nl per dose. In some embodiments, the cells administered in a volume of about 10, about 20, about 30, about 40, about 50, about 60, about 70, about 80, about 90, about 100, about 200, about 300, about 500, or about 1000 µl per dose.

In some embodiments, a single dose is administered over the course of about 1 minute, about 2 minutes, over the course of about 3, 4, 5, 6, 7, 8, 9, 10, 15, 20, 25, 30, 45, or 60 minutes. In some embodiments, a single dose is administered over the course of about 1 hour, 2 hours, 3 hours, 4 hours, 5 hours, or 6 hours.

In some embodiments, the cells are treated prior to administration with one or more cell differentiation factors.

In some embodiments, the neural precursor cells disclosed herein are capable of functionally integrating into the endogenous host neural network, for example, functionally integrating into the neural network of the arcuate nucleus in the hypothalamus, and/or into structures immediately adjacent to or surrounding the arcuate nucleus, such as, but not limited to the mediobasal hypothalamus and the ventromedial hypothalamus. In some embodiments, the precursor cells, once administered and integrated, exhibit one or more of the following activities: show spontaneous firing activity; show spontaneous excitatory postsynaptic currents (sEPSCs); receive synaptic glutamatergic inputs from neighboring host cells. In some embodiments, sEPSCs are blocked by glutamatergic receptor antagonist AP5 and CNZX. In some embodiments, the functional integration of the administered cells is confirmed by a decrease in the blood glucose level of the subject.

Methods of determining blood glucose levels are well known in the art, and numerous tests, monitors, meters, kits, and systems are available. In some embodiments, a subject's blood glucose level is monitored for a time prior to treatment. By way of example, in some embodiments, a subject's glucose level is monitored for a matter of weeks, months, or even years prior to treatment, and is determined to be, on average, above the normal range as compared to an appropriate control (i.e., the subject is said to be hyperglycemic). After treatment according to the methods disclosed herein (e.g., after administration of MGC precursor cells into the arcuate nucleus of the subject), the subject's glucose levels decrease by a statistically relevant amount.

In some embodiments, the subject's glucose level shows a statistically significant decrease within about 2 days, about 3 days, about 4 days, about 5 days, about 6 days, about 7 days, or within about 2 weeks after administration of the inhibitory neuronal precursor cells into the arcuate nucleus of the subject. In some embodiments, the subject's glucose levels are decreased by about 5%, by about 10%, by about 15%, by about 20%, by about 25%, by about 30%, by about 35%, or by about 40% or more as compared to the subject's pre-treatment glucose levels. For example, while the subject's glucose levels may fluctuate throughout the day, or may fluctuate in response to diet, exercise, etc., the fluctuations are within a lower average range overall as compared to pre-treatment fluctuations and average ranges (e.g., the high levels are lower than pre-treatment high levels, or the high levels decrease more quickly than the pre-treatment high levels). In some embodiments the decreased glucose level is considered a chronic change, and the lower glucose range(s) persist for weeks, months, or years.

Methods of administering the MGE precursor cells of the present disclosure to animals, particularly humans, include injection or implantation of the MGE precursors cells into the arcuate nucleus and/or into structures immediately surrounding, or adjacent to the arcuate nucleus, such as the mediobasal hypothalamus, including the ventromedial hypothalamus. Accordingly, in exemplary embodiments, the compositions and/or cells of the disclosure can be inserted into a delivery device which facilitates introduction by, for example, injection or implantation, of the cells into the brain. Such delivery devices include needles, syringes, and tubes, such as catheters, for injecting cells and fluids into the body of a recipient.

In some embodiments, the tubes have a needle, e.g., a syringe, through which the cells can be introduced into the animal at a desired location. The MGE precursor cells can be inserted into such a delivery device in different forms. For example, the cells can be suspended in a solution or embedded in a support matrix when contained in such a delivery device. As used herein, the term "solution" includes a pharmaceutically acceptable carrier or diluent in which the cells remain viable. Pharmaceutically acceptable carriers and diluents include saline, aqueous buffer solutions, solvents and/or additional media that are well known in the art. The solution is preferably sterile and fluid to the extent that easy syringability exists.

Methods to identify and target specific brain structures are well known in the art. When the cells are implanted into the brain, stereotaxic methods may be used as described in Leksell and Jernberg, Acta Neurochir., 52:1-7 (1980) and Leksell et al., J. Neurosurg., 66:626-629 (1987), both of which are incorporated herein by reference. Localization of target regions may include pre-implantation MRI as described in Leksell et al., J. Neurol. Neurosurg. Psychiatry, 48:14-18 (1985), incorporated herein by reference. Target coordinates can be determined from the pre-implantation MRI.

Additionally or alternatively, brain structures may be imaged e.g., via CT scan or MRI. By way of example, brain structures may be imaged during MRI by a technique known as Diffusion Tensor Imaging (DTI), and a particular brain structure can be identified by its afferent or efferent connections with other brain structures, by reference to other brain structures or by their proximity to other brain structures. That is, for example, by imaging the hypothalamus using DTI MRI, nerve tracts can be identified and followed and used as landmarks or pathways to help identify the target brain region or brain structure. After identifying the brain structure(s) by following the nerve tract(s) to the brain structure(s) and selecting a reference, the exact position of the brain structure/target area can be coded into three-dimensional (3D) coordinates. The information obtained from the DTI MRI can also be used to plan the trajectory or angle of implantation of an electrode, marker, or therapeutic cells, such that surrounding tracts and vasculature may be avoided. These 3D coordinates can be used to insert a cannula, needle, etc., to deliver a therapy (e.g., MGE precursor cells) to the brain structure (e.g., arcuate nucleus of the hypothalamus and/or surround structures such as the mediobasal hypothalamus including the ventromedial hypothalamus).

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

EXAMPLES

Non-Limiting Examples of Treatment of Diabetes in Mammals

Example 1: Preparation and Exemplary Methods

Interneuron Harvest

Inhibitory interneuron precursors were derived by acutely dissecting the medial ganglionic eminence (MGE) from the brain of embryonic day 13.5 (E13.5) or E14.5 GAD67-GFP transgenic embryos. These transgenic mice express green fluorescent protein (GFP) in inhibitory interneurons, allowing the neurons to be tracked. After dissection, the MGE explants were triturated in serum-free media to single cell suspension, centrifuged down to concentrate the suspension, and placed on ice until grafting.

Arcuate Nucleus Transplantation

MGE cells were loaded into pulled glass micropipettes secured to a micromanipulator on a custom-built stereotaxic rig used for mouse intracerebral injections. Leptin-deficient ob/ob mice, a widely-used model of type 2 diabetes, were positioned within the stereotaxic rig, a midline incision made in the scalp, and bregma was identified as the zero-reference coordinate for stereotaxy. The arcuate nucleus was targeted at coordinates 0.25 mm lateral, 0.6 to 0.8 mm anterior-posterior, and 5.7 mm deep, with a burrhole drilled at the appropriate skull position for intracranial access. A volume of about 20 to 50 nanoliters of cell suspension was then injected slowly over the course of 1-2 minutes.

Metabolic Phenotyping

Ob/ob mice were single-housed and evaluated prior to enrollment in the study to ensure they had diabetic range hyperglycemia (blood glucose 175-350 mg/dl) and that experimental and control groups were matched for blood glucose, body weight, and food intake. Measures of blood glucose (using Aviva Accucheck glucose test strips and glucometer), body weight, and food intake were made in the morning 3 hours after "lights-on" (~9 am). After transplantation, the mice were maintained in single housing and we continued to make these measures for one month prior to sacrificing the mice for histology.

Results

MGE interneurons derived from E13.5 GAD67-GFP embryos and transplanted bilaterally into the ob/ob ARC survive, integrate into local circuits, and form GABAergic synapses. Metabolic phenotyping shows that compared to vehicle injection, transplanted MGE cells (~10,000 MGE cells/ARC for 20 nl graft) induce a sustained reduction of hyperglycemia lasting for at least one month (1-month average BG: veh 301±12 vs. MGE 189±12 mg/dl, n=4/group, p=0.022) without significant effects on food intake or body weight (see FIG. 1). These findings suggest that sustained diabetes treatment, e.g., remission, can be achieved by remodeling ARC neurocircuits through MGE cell transplantation.

Example 2

Common methods of administering the MGE precursor cells of the present disclosure to animals, particularly humans, include injection or implantation of the MGE precursors cells into the arcuate nucleus. Accordingly, in exemplary embodiments, the cells of the disclosure can be inserted into a delivery device which facilitates introduction by, for example, injection or implantation, of the cells into the brain. Such delivery devices include tubes, such as catheters, for injecting cells and fluids into the body of a recipient.

In some embodiments, the tubes additionally have a needle, e.g., a syringe, through which the cells can be introduced into the animal at a desired location. The MGE precursor cells can be inserted into such a delivery device in different forms. For example, the cells can be suspended in a solution or embedded in a support matrix when contained in such a delivery device. As used herein, the term "solution" includes a pharmaceutically acceptable carrier or diluent in which the cells remain viable. Pharmaceutically acceptable carriers and diluents include saline, aqueous buffer solutions, solvents and/or additional media that are well known in the art. The solution is preferably sterile and fluid to the extent that easy syringability exists.

When the cells are implanted into the brain, stereotaxic methods will generally be used as described in Leksell and Jernberg, Acta Neurochir., 52:1-7 (1980) and Leksell et al., J. Neurosurg., 66:626-629 (1987), both of which are incorporated herein by reference. Localization of target regions will generally include pre-implantation MRI as described in Leksell et al., J. Neurol. Neurosurg. Psychiatry, 48:14-18 (1985), incorporated herein by reference. Target coordinates will be determined from the pre-implantation MRI.

Prior to implantation, the viability of the cells may be assessed by the following method. Briefly, sample aliquots of the cell suspension (1-4 µl) are mixed on a glass slide with 10 µl of a mixture of acridine orange and ethidium bromide (3.4 g/ml of each component in 0.9% saline; Sigma). The suspension is transferred to a hemocytometer, and viable and non-viable cells are visually counted using a fluorescence microscope under epi-illumination at 390 nm combined with white light trans-illumination to visualize the counting chamber grid. Acridine orange stains live nuclei green, whereas ethidium bromide will enter dead cells resulting in orange-red fluorescence. Cell suspensions may generally contain more than about 98% viable cells.

In humans, the following exemplary methods may be utilized. Injections will generally be made with sterilized 10 µl Hamilton syringes having 23-27 gauge needles. The syringe, loaded with cells, is mounted directly into the head of a stereotaxic frame. The injection needle is lowered to predetermined coordinates through small burr holes in the cranium, about 40-50 µl of suspension (wherein "about" means+/−10% of the stated value) are deposited at the rate of about 1-2 µl/minute and a further 2-5 minutes are allowed for diffusion prior to slow retraction of the needle. Frequently, two or more separate deposits will be made, separated by 1-3 mm, along the same needle penetration, and up to 5 deposits scattered over the target area can readily be made in the same operation. The injection may be performed manually or by an infusion pump. At the completion of surgery following retraction of the needle, the patient is removed from the frame and the wound is sutured. Prophylactic antibiotics or immunosuppressive therapy may be administered as needed.

According to the present disclosure there is provided a method of increasing inhibitory neuron activity in the host central nervous system in a mammal, comprising transplanting MGE cells into the arcuate nucleus of the brain of that mammal. In particular, the method is for modifying inhibition in the brain, such as for treatment of diabetes.

The transplanted cells may be sourced in any way known in the art, for example, isolations from living or deceased organisms, from in vitro sources such as tissue culture, and the like.

While the preferred embodiments of the present technology have been illustrated in detail, it should be apparent that modifications and adaptations to those embodiments may occur to one skilled in the art without departing from the scope of the present technology.

I claim:

1. A method for the treatment of a mammal having pre-diabetes or diabetes, comprising: administering an effective amount of mammalian MGE (medial ganglionic eminence) precursor cells to one or more of an arcuate nucleus of the hypothalamus region of the brain, the mediobasal hypothalamus region of the brain, and the ventromedial hypothalamus region of the brain, wherein the mammalian MGE precursor cells form interneurons that functionally integrate with endogenous neurons such that an improvement in the symptoms of prediabetes or diabetes in the treated mammal is achieved.

2. The method of claim 1, wherein the mammalian MGE precursor cells are administered by injection.

3. The method of claim 1, wherein the mammalian MGE precursor cells are administered through transplantation with a catheter or needle.

4. The method of claim 1, wherein the mammal has diabetes.

5. The method of claim 4, wherein the diabetes is type 2 diabetes.

6. The method of claim 1, wherein between about 20 nanoliters to 50 microliters of a suspension comprising the mammalian MGE precursor cells is administered.

7. The method of claim 1, wherein the mammalian MGE precursor cells are embryonic MGE precursor cells.

8. The method of claim 1, wherein the mammalian MGE precursor cells are cultured MGE precursor cells.

9. The method of claim 1 wherein the mammal is a human.

10. The method of claim 1, wherein administration is to the arcuate nucleus of the hypothalamus region of the brain.

* * * * *